United States Patent [19]

Lukacsko et al.

[11] Patent Number: 4,965,065

[45] Date of Patent: Oct. 23, 1990

[54] GASTROPROTECTIVE PROCESS AND COMPOSITIONS

[75] Inventors: Alison B. Lukacsko, Robbinsville; Randy J. Koslo, East Windsor, both of N.J.

[73] Assignee: Bristol-Myers Squibb Company, New York, N.Y.

[21] Appl. No.: 11,792

[22] Filed: Feb. 6, 1987

Related U.S. Application Data

[63] Continuation-in-part of Ser. No. 858,542, Apr. 29, 1986, abandoned, which is a continuation of Ser. No. 836,263, Mar. 4, 1986, abandoned.

[51] Int. Cl.$^5$ .................. A61K 31/615; A61K 31/60; A61K 31/225
[52] U.S. Cl. ..................................... 424/10; 514/162; 514/165; 514/548; 514/568; 514/653
[58] Field of Search ............... 514/165, 162, 548, 653, 514/568; 424/10

[56] References Cited

U.S. PATENT DOCUMENTS 4,579,846 4/1986 Crawford et al. .................. 514/450

OTHER PUBLICATIONS

W. S. Colucci, et al., New England, J. Med., 305:185-190 (1981).
K. Weber, et al., Circulation, 66:1262-1267 (1982).
Fielding, et al., Effect of Salbumatol [SiC] on Acute Gastric Ulceration Induced by Indomethacin in the Rat, Eur. Surg. Res., 9:252-7 (1977).
Kasuya, et al., Effects of Various Drugs and Vagotomy on Indomethacin-Induced Gastric Ulcers in the Rat, Japan. J. Pharmacol., 29:670-3 (1979).
McGreevy, et al., The Protection of Gastric Mucosa Against Aspirin-Induced Erosions by Enhanced Blood Flow, Surg. Forum, 28:357-359 (1977).
Goodman et al., *The Pharmacological Basis of therapeutics*, 5th Ed. (1975), p. 481.
*The Merck Index*, 10th Ed. (1983), p. 712.

*Primary Examiner*—Douglas W. Robinson
*Attorney, Agent, or Firm*—Charles Zeller

[57] ABSTRACT

A pharmaceutical composition and process for administering non-steroidal anti-inflammatory drugs which are protected against injury to gastrointestinal tract by beta adrenergic agonists.

30 Claims, No Drawings

GASTROPROTECTIVE PROCESS AND COMPOSITIONS

This is a continuation-in-part of application Ser. No. 858,542, filed on Apr. 29, 1986, which is a continuation of application Ser. No. 836,263, filed on Mar. 4, 1986, now abandoned.

This invention relates to non-steroidal ant-inflammatory drug (hereinafter referred to as NSAID) composition containing protectants against gastrointestinal injury induced by such NSAIDs and to processes for administering such composition. More particularly it concerns compositions and processes of the aforesaid type that employ beta adrenergic agonists as the protectants. The compositions of this invention are useful in treating conditions and symptoms that are classically treated by the administration of NSAIDs e.g. headache pain, pain and inflammation associated with arthritis and other systemic diseases, elevated body temperatures etc.

This invention also relates to a process for inhibiting gastric acid secretion and the treatment of peptic ulcers.

Aspirin and other NSAIDs have long been the most popular drugs for the management of pain, inflammation and fever. However, one of the drawbacks in their use is the gastrointestinal injury and/or bleeding that sometimes accompanies their administration to individuals. This may become a particularly severe problem where large and sustained doses of NSAIDs must be given to control the symptoms, as for example, in the case of the management of arthritis.

It has now been found that NSAID induced gastrointestinal injury and particularly gastrointestinal mucosal injury can be significantly reduced when beta adrenergic agonists are administered concurrently with a NSAID. The beta adrenergic agonists form a fairly well defined class of pharmaceutically effective compounds that are characterized by the fact that they act by stimulating beta adrenergic receptor sites. These receptor sites are of two types referred to as the beta 1 and beta 2 sites. Beta adrenergic agonists may act on one or the other or on both types of sites. Any of these are effective in practicing the present invention.

It has also been found that gastric acid secretion can be inhibited, and peptic ulcers can be treated by the administration of a beta adrenergic agonist. Typical agonists of this type which can be used in accordance with the invention, include isoproterenol, metaproterenol, terbutaline, albuterol, fenoterol, bitolterol, isoetharine, colterol, or ritodrine or their pharmaceutically acceptable salts.

A number of beta adrenergic agonists are known in the prior art which are useful for the purposes of this invention. Of special interest are isoproterenol which is a mixed beta 1 and beta 2 agonist and terbutaline which is a beta 2 agonist. By way of illustrating other beta adrenergic agonists that may be employed herein, the following are given metaproterenol, albuterol, ritodrine. All of these may be employed as such or as pharmaceutically acceptable salts.

The NSAIDs also form a well known class of drugs that are anti-inflammatory analgesics. These have the common property of inhibiting the formation of prostaglandins which have a protective affect on the gastrointestinal mucosa. See Goodman and Gilman "The Pharmacological Basis for Therapeutics" 7th Edition, p. 678. It is because of this inhibiting effect that the oral administration of drugs of this class tend to result in gastrointestinal injury and/or bleeding, the problem that the present invention seeks to reduce or eliminate.

A number of NSAIDs are known in the prior art to which the present invention has application. The most commonly known group are the salicylates of which aspirin is the prime example. Another group of NSAIDs that have utility in connection with the instant invention are the proprionic acid derivatives. Included in this group, for example, are ibuprofen and naproxen. A further group of NSAIDs employable herein are the fenamates and compounds closely related to them structurally. These may be illustrated by such compounds as mefenamic acid, meclofenamate sodium, diclofenac and its sodium salt. Also belonging to the class of NSAIDs with which the present invention is concerned are the indole derivatives (e.g. indomethacin); pyrrolealkanoic acid derivatives (e.g. tolmetin); pyrazalone derivatives (e.g. phenylbutazone); oxicams (e.g. piroxicam); etc.

The quantitative relationship of the NSAID to beta adrenergic agonist contained in the present products may be expressed on the basis of the average daily dose of the product i.e. milligrams/per Kg of body weight/per day. In this case the average dose for the products will generally be from about 10 mg/Kg/day to about 100 mg/Kg/day of NSAID and from about 0.0003 mg/Kg/day to about 500 mg/Kg/day of one or a combination of beta adrenergic agonists with the preferred range being from about 15 mg/Kg/day to about 75 mg/Kg/day of NSAID and from about 0.01 mg/Kg/day to about 10 mg/Kg/day of said beta adrenergic agonists.

The unit dosage forms for the present products will be formulated for convenient oral administration. Each such unit will generally contain from about 200 mg to about 600 mg of NSAID and from about 0.7 mg to about 70 mg of one or a combination of adrenergic agonists.

Depending upon the dosage form employed the products of this invention may also contain other adjuvants that may be useful in formulating the particular dosage form or in its administration. Thus, for example, when administered as a tablet the products of this invention may also contain lubricants, excipients, binding agents, disintegrating agents, flavoring agents, etc. In addition these products may also contain other pharmaceutically active ingredients such as decongestants, analgesic adjuvants, antihistamines, expectorants, antitussives, diuretics, other analgesics, other anti-inflammatory agents, other antipyretics, other antirheumatics, antioxidants, vasodilators, smooth muscle relaxants, skeletal muscle relaxants, bronchodilators, vitamins, trace minerals, amino acids, biological peptides etc.

For therapeutic use the beta adrenergic agonist will normally be administered as a pharmaceutical composition comprising as the essential active ingredient at least one of such agonist in its basic form or in the form of a non-toxic pharmaceutically acceptable acid addition salt, in association with a pharmaceutically acceptable carrier. The pharmaceutical composition can be administered orally intranasally, parenterally, or by rectal suppository. A wide variety of pharmaceutical forms may be employed. Thus, if a solid carrier is used, the preparation may be a tablet, placed in a hard gelatin tabsule in powder or granular form, or in a form of a troche, caplet or capsule. If a liquid carrier is employed, the preparation may be in a form of a syrup, emulsion, soft gelatin capsule, sterile solution for injection, or an aqueous or non-aqueous liquid suspension. The pharmaceutical compositions are prepared by conventional techniques appropriate to the desired preparation.

The dosage of the compositions of this invention will depend not only on such factors as the weight of the patent, but also in the degree of gastric acid inhibition desired and the potency of the particular compound being utilized. The decision as to the particular dosage to be employed is within the discretion and the routine knowledge of the physician. In the Heidenhain Pouch Dog test described below, cimetidine has an oral $ED_{50}$ of approximately 3.3 $\mu$ moles/kg. The usual human adult oral dose of cimetidine is 300 mg, given four times a day. The usual human adult starting oral dosages of the compounds of this invention are readily determined from their oral $ED_{50}$ in this same test. Thus, if the oral $ED_{50}$ is 0.33 $\mu$ moles/kg. The usual starting oral dosage would be approximately 30 mg. given four times a day, etc. Similar calculations may be made for intravenous dosages. These starting dosages (and the number of times administered per day) may, of course, be varied by titration of the dosage to the particular circumstances of the specific patient. With the preferred compounds of this invention, each oral dosage unit will contain the active ingredient in an amount of from about 0.5 mg. to about 300 mg. and mostly preferably from about 1.0 mg to about 100 mg. The active ingredient will preferably be administered in equal doses from one to four times a day.

Depending upon the dosage form employed the products of this invention may also contain other adjuvants that may be useful in formulating the particular dosage form or in its administration. Thus, for example, when administered as a tablet the products of this invention may also contain lubricants, excipients, binding agents, disintegrating agents, flavoring agents, etc. In addition these products may also contain other pharmaceutically active ingredients such as decongestants, analgesic adjuvants, antihistamines, expectorants, antitussives, diuretics, other analgesics, other anti-inflammatory agents, other antipyretics, other antirheumatics, antioxidants, vasodilators, smooth muscle relaxants, skeletal muscle relaxants, bronchodilators, vitamins, trace minerals, amino acids, biological peptides etc.

The products of this invention may take a variety of forms. As indicated above they may assume the form of tablets. However, the NSAID and the beta adrenergic agonists may be in powdered or granular form contained in edible capsules such as gelatin capsules. The present products may also take the form of suspensions or solutions of the above ingredients in a suitable liquid medium or of powders packaged in suitable paper envelopes.

The mechanism by which the beta adrenergic agonists serve as protectants against gastrointestinal injury when administered as the sole pharmaceutically active ingredient, or coadministered with the NSAID is not clearly understood. One factor seems fairly certain and that is that it is not necessarily simply related to the inhibition of gastric acid secretion. This is made evident by the observation that, for example, with certain levels of isoproterenol, gastric injury protection has been noted notwithstanding the fact that the pH of the stomach content was essentially the same as the pH of the control stomach. Similarly, as reported by M.H. Steven et al in the Abstract of Papers; "Gastroenterology" Vol. 88, No. 5 Part 2 at page 1600, although isoproterenol had a role in the regulation of gastric secretion stimulated by gastrin and acetylcholine, histamine-stimulated acid secretion was resistant to inhibition by isoproterenol. In passing, it might be noted that Steven et al were not measuring the effect of the coadministration of aspirin with isoproterenol.

DETERMINATION OF GASTRIC ANTISECRETORY ACTIVITY IN THE GASTRIC FISTULA RAT

Male Long Evans rats weighing about 240–260 grams at the time of cannula implementation are used. The design and implementation of the stainless steel cannula into the anterior wall of the fore-stomach are carried out essentially as described by Pare et al. (Laboratory Animal Science, 27, 244 (1977). The fistula components are designed and the operative procedure is carried out exactly as described in the above reference. Post operatively the animals are individually housed in solid bottom cages with sawdust and are allowed food and water ad libitum throughout the entire recovery period. Animals are not used for test purposes for at least 15 days after the operative procedure.

The animals are fasted but allowed water ad libitum for 20 hours before the testing procedure is to begin. Immediately prior to collection, the cannula is opened and the stomach washed gently with 30–40 ml of warm saline or distilled water to remove any residual contents. The catheter is then screwed into the cannula in place of the plugging screw and the rat is placed in a clear plastic rectangular cage measuring 40 cm long, 15 cm wide and 13 cm high. The bottom of the cage has a slit approximately 1.5 cm wide and 25 cm long running down the center to accommodate the catheter which hangs through it. In this way the rat is not restricted and can move freely about the cage during collection periods. The remainder of the assay is carried out as described by Ridley et al. [Research Comm. Chem. Path. Pharm., 17, 365 (1977)].

Gastric secretions collected during the first hour after washing the stomach are discarded as they may be contaminated. For oral evaluation, the catheter is then removed from the cannula and replaced with the plugging screw. Water (2 ml/kg) is administered orally via gastric intubation and the animal is returned to the cage for 45 minutes. After this time the plugging screw is removed and replaced with a catheter to which a small plastic vial has been attached to collect the gastric secretions. A two hour sample is collected (this represents the control secretion), the catheter removed and replaced with the plugging screw. The test drug is now administered orally in a volume of 2 ml/kg via gastric intubation. Forty-five minutes later the plugging screw is again removed, replaced with the catheter attached to a small plastic vial and another 2 hour sample is compared to those of the control sample in order to determine the effects of the test drug.

When test compounds are to be evaluated parenterally, the animal is injected Ip or sc with the test compound vehicle in a volume of 2 ml/kg immediately after discarding the initial 60 minute collection. A two hour sample is collected (control secretion) and the animals are injected either ip or sc with the test compound in a volume of 2 ml/kg. An additional two hour sample is collected and its secretions are compared to those of the control period to determine drug effects.

The samples are centrifuged and placed in a graduated centrifuge tube for volume determination. Titratable acidity is measured by titrating a one ml sample to pH 7.0 with 0.2N NaOH, using an autoburet and an electrometric pH meter (radiometer). Titratable acid output is calculated in microequivalents by multiplying the volume in milliliters by the acid concentration in milliequivalents per liter.

Results are expressed as percent inhibition relative to control reading. Dose response curves are constructed and $ED_{50}$ values are calculated by regression analyses. At least three rats are used at each dosage level and a minimum of three dosage levels are utilized for determination of a dose responsive curve.

Two of the standard animal models for determining gastric antisecretory activity of antagonists are the Gastric Fistula Rat and the Heidenhain Pouch Dog. Comparative data between metaproterenol, a known beta adrenergic agonist, and cimetidine, a known $H_2$ receptor antagonist and effective inhibitor of gastric secretion, is shown in tables I and II below:

TABLE I

| Gastric antisecretory activity in the Gastric Fistula Rat $ED_{50}$ values (mg/kg) for oral treatment | | |
|---|---|---|
| Metaproterenol | Cimetidine | Potence Ratio (Cimetidine = 1) |
| 23.6 (15–42)* | 12 (9.0–18)* | 0.58 |

*(95% confidence limit)

DETERMINATION OF GASTRIC ANTISECRETORY ACTIVITY IN THE HEIDENHAIN POUCH DOG

Prior to surgery, hematology and blood chemistry profiles are obtained and an assessment made as to the general health of selected female dogs. Dogs are vaccinated with Tissue Vax 5 (DHLP-Pitman-Moore) and housed in general animal quarters for an observation period of four weeks, so incipient diseases may become apparent. Dogs are fasted with water ad libitium 24 hours prior to surgery.

Anesthesia is induced with sodium pentothal (Abcott ) 25–30 mg/kg iv. Subsequent anesthesia is maintained with methoxyflurane (Pitman-Moore). A midline linea alba incision from xiphoid to umbilcus provides good exposure and ease of closure. The stomach is pulled up into the operative field, the greater curvature stretched out at multiple points and clamps placed along the selected line of incision. The pouch is made from the corpus of the stomach so that true parietal cell juice is obtained. About 30% of the corpus volume is resected. The cannula is made of light-weight, biologically-inert material such as nylon or Delrin with dimensions and attachments after DeVito and Harkins [J. Appl. Physiol., 14, 138 (1959)]. Post operatively, dogs are medicated with antibiotics and an analgesic. They are allowed 2–3 months for recovery. Experiments are carried out in the following way: Dogs are fasted overnight (18 hours) with water ad libitum prior to each experiment. The dogs are placed in a sling and a saphenous vein cannulated for drug administration. Histamine as the base (100 µg/kg/hr) and chlorpheniramine maleate (0.25 mg/kg/hr) are infused continuously (in a volume of 6 ml/hr) with a Harvard infusion pump.

A Ninety minute infusion is allowed for the dogs to reach a steady state of acid output. At this time the drug or normal saline (control) is administered concomitantly with the secretagogue in a volume of 0.5 ml/kg over a 30 second period. When oral studies are to be carried out, the drug is administered via gastric gavage in a volume of 5 ml/kg. Infusion of the secretagogue is continued and 15 minute samples of the gastric juice are taken for 4.5 hours. Each sample is measured to the nearest 0.5 ml and titratable acidity is determined by titrating a 1 ml sample to pH 7.0 with 0.2N NaOH, using an autoburet and an electrometric pH meter (or radiometer). Titratable acid output is calculated in microequivalents by multiplying the volume in milliliters by the acid concentration in a millequivalents per liter.

Results are expressed as percent inhibition relative to control readings. Dose response curves are constructed and $ED_{50}$ values are calculated by regression analyses. From 3 to 5 dogs are used at each dose level and a minimum of three dosage levels are utilized for determination of a dose response curve.

TABLE II

| Gastric Antisecretory Activity in the Heidenhain Pouch Dog $ED_{50}$ values (mg/kg for oral treatment) | | |
|---|---|---|
| Metaproterenol | Cimetidine | Potency Ratio (Cimetidine = 1) |
| 0.05 | 0.71 | 14.2 |

Cytoprotective activity was evaluated in five test models. Metaproterenol was compared to cimetidine as a protectant. The term "cytoprotection" describes the phenomenon whereby some agents protect the gastric mucosa against injury induced by a variety of injurious stimuli. These assays are primarily used as secondary models to evaluate agents which have confirmed antigastric secretory activity and/or activity in primary (antisecretory) models. In the present case, the beta adrenergic agonist metaproterenol was compared to the cytoprotective activity of cimetidine. The injurious stimuli in our present test were provided by ethyl alcohol, aspirin and stress, hydrochloric acid, and indomethacin. The respective assays were carried out as described below:

Ethyl alcohol:

The method employs 3.0 ml/kg ethyl alcohol (100%) as the necrotizing agent and provides additional data besides gastric lesions.

Adult male Long-Evans rats weighting 275–300 grams (Blue Spruce Farms, Alton, N.Y.) are used. Animals are housed individually in stainless steel cages with wire-mesh bottoms. The housing battery is arranged into six groups of five each, individually numbered. Food and water are removed 24 and 1 ½ hours, respectively, prior to exposure to ETOH. Animals receive the test compound either p.o., s.c., or i.p. (3–12 ml/kg) 60 minutes before administration of 100% ethanol (3.0 ml/kg/ by gavage). For some purposes, different water removal and drug pretreatment times may be used. Sixty minutes after ethanol administration the animals are sacrificed by administration of T-61 (Hoechst), 0.2 ml i.p.

An abdominal incision is made, and after clamping the esophagus just above the esophageal sphincter with forceps, the stomach is carefully lifted from the abdominal cavity. Two cuts are made, approximately ¼" below the pyloric valve and ¼" above the esophageal sphincter, and the stomach removed rapidly without any loss of gastric contents. The size of the stomach including contents is noted as small, medium or large. Stomachs are cut open along the greater curvature and the contents expressed into graduated centrifuge tubes. Gastric juice samples are centrifuged and total volume, and contents of solids and mucus are estimated to the nearest 0.1 ml Na+ and K+ content of the gastric juice as well as pH are determined.

Under these conditions, ethanol produces prominent macroscopic lesions in the fundic stomach, but gross macroscopic changes are only very rarely observed in the forestomach. An occasional control animal shows some degree of redness or hyperemia and/or smell petechiae in the forestomach. Lesions characteristic of fundic damage are not usually observed. For these reasons, the forestomach (along with nongastric tissue) is removed and not examined. In addition, absence of the forestomach facilitates the photocopy and gross examination of the remaining stomach.

The remaining fundic-pyloric stomach remnant is rinsed in water and placed flat in a standard position. The tissue is photographed with a Polaroid camera with a close-up lens. Scoring of lesions is done from this permanent record. Each photograph includes a reference scale in mm. Individual ulcers are measured by total lesion are (mm$^2$) and these scores are added together to determine total ulcer area for a stomach. Small well defined but quite visible spots (petechiae) are often present; a conglomerate area estimate is made for these and added to the total. Some variability in ulcer scoring between persons may occur because even optimal quality photographs will show minor shadows, shades, overexposed spots and irregularly shaped ulcers.

Standard photographs are about 2 X actual size. An estimate of real ulcer area (mm$^2$) is obtained after dividing the area score by four. For each treatment group, the mean area is calculated. From this, the percent inhibition of lesion formation, I is calculated as:

$$I = \frac{\text{Lesion Score (controls)} - \text{Lesion Score (treated)}}{\text{Lesion Score (Controls)}} \times 100$$

The mean ulcer score for a control group will be used to calculate "I" but normally individual lesion scores are used in drug treatment groups. In some cases, the observed treatment score is greater than the mean control valve, in which case that score is taken as the mean control valve (exacerbation of lesion formation is not considered). In rare instances, the data from an animal will be discarded if, e.g., feces are found in the stomach.

In dose-response studies, the ED$_{50}$ (dose at which 50% inhibition of lesion formation occurs) is determined by probit analysis.

Aspirin + Stress

Male Long Evans rate (approximately 275-300 gms) are housed 6 per cage and acclimated at least three days while maintained on an ad libitum schedule of food and water. Prior to starting an experiment, rats are deprived of food for twenty-four hours and water for one hour. Thirty minutes before subjecting animals to cold restraint stress, each rat is dosed by gastric intubation (6 ml/kg) with aspirin (80 mg/kg) homogenized with methy-cellulose (0.1%) in water. Test agents are administered 60 or 30 min prior to the aspirin mixture either orally or parenterally. Each control of drug treated group normally consists of 5 rats. The multi-stress method entails placing the dosed rat in a ventilated plastic tube closed at one end with a rubber stopper. The open end is then closed with a second stopper and the tube is place in an environmental chamber maintained at 4°-5° C for two hours. The tube contains several $\frac{3}{8}$" holes for breathing purposes and is about ten inches long and two inches wide. At the end of the two-hour cold-restraint period, each animal is sacrificed with an injection of T-61 euthanasia solution (Hoechst).

* An abdominal incision is made and the stomach removed by cutting just above the esophageal sphincter and just below the pyloric valve. The stomach is opened along the greater curvature and the stomach contents discarded. Under the conditions described, aspirin plus cold restraint stress produces spotty and narrow dark bands of linear macroscopic lesions which are usually found in the corpus fundic stomach. Therefore, forestomach and other accessory tissue which show no macroscopic lesion damage are trimmed. The remaining fundic portion is rinsed with water and placed flat in a standard position for photographing. The stomach along with a millimeter reference scale is photographed at 2X actual size with a Polaroid camera. Scoring of lesions is done from this permanent record.

The lesion score is determined by measuring and adding together the total millimeter lengths of all visible erosions. Small spots (petechia) are scored as 1.0 mm each and added to the aggregate. An estimate of real lesion length is obtained by dividing the aggregate score by two. For each treatment group, a mean lesion score is determined. From this, the percent inhibition of lesion formation, I, is calculated as:

$$I = \frac{\text{Lesion Score (controls)} - \text{Lesion Score (treated)}}{\text{Lesion Score Controls}} \times 100$$

The mean lesion score for a control group will be used to calculate "I" but individual lesion scores will usually be used in drug treatment groups. Observed treatment scores that exceed the mean control value are taken as the mean control value without considering exacerbation of lesion formation.

In dose response studies, the ED$_{50}$ (dose at which 50% inhibition of lesion formation occurs) is determined by probit analysis.

HCl:

The present method to produce gastric lesions in rats employs 3.0 ml/kg 0.75N HCl as the necrotizing agent and provides additional data besides gastric lesions.

Adult male Long-Evans rats weighing 2.75-300 grams (Blue Spruce Farms, Alton, N.Y.) are used. Animals are housed individually in stainless steel cages with wire-mesh bottoms. The housing battery is arranged into six groups of five each, individually numbered. Food and water are removed 24 and 1 $\frac{1}{2}$ hours, respectively, prior to HCl. Animals receive the test compounds either p.o., s.c., or i.p. (3-12 ml/kg) 60 minutes before administration of 0.75N HCl (3.0 ml/kg/ by gavage). For some purposes, different water removal and drug pretreatment times may be used. Sixty minutes after HCl the animals are sacrificed by administration of T-61 (Hoechst), 0.2 ml i.p.

An abdominal incision is made, and after clamping the esophagus just above the esophageal sphincter with tweezers, the stomach is carefully lifted from the abdominal cavity. Two cuts are made, approximately $\frac{1}{4}$" below the pyloric valve and $\frac{1}{4}$" above the esophageal sphincter, and the stomach rapidly removed without any loss of gastric contents. The size of the stomach including contents is noted as small, medium or large. Stomachs are cut open along the greater curvature and the contents expressed into graduated centrifuge tubes. Gastric juice samples are centrifuged and total volume, and contents of solids and mucus are estimated to the nearest 0.1 ml. Na+ and K+ contents of the gastric juice as well as pH are determined.

Under these conditions 0.75N HCl produces prominent macroscopic lesions in the fundic stomach; but gross macroscopic changes are only very rarely observed in the forestomach. An occasional control animal shows some degree of redness or hyperemia and/or small petechiae in the forestomach, but never lesions characteristic of fundic damage. For these reasons, the forestomach (along with nongastric tissue) is removed and not examined. In addition, absence of the forestomach facilitates the photography and examination of the remaining stomach. Wet weight of the whole stomach is determined before removal of the forestomach.

The remaining fundic-pyloric stomach remnant is rinsed in water and placed flat in a standard position. The tissue is photographed with a Polaroid camera with a close-up lens. Scoring of lesions is done from this permanent record. Each photograph includes a reference scale in mm. Individual ulcers are measured by total lesion length in mm and these scores are added together to determine total ulcer length for a stomach. Small well defined but quite visible spots (petechiae) are often present; a conglomerate length estimate is made for these and added to the total. Some variability ulcer scoring between persons may occur because even optimal quality photographs will show minor shadows, shades, overexposed spots and irregularly shaped ulcers.

Standard photographs are about 2 X actual size. An estimate of real ulcer length (mm$^2$) is obtained after dividing the length score by two. For each treatment group, the mean length is calculated. From this, the percent inhibition of lesion formation, I is calculated as:

$$I = \frac{\text{Lesion Score (controls)} - \text{Lesion Score (treated)}}{\text{Lesion Score (controls)}} \times 100$$

The mean ulcer score for a control group will be used to calculate "I" but normally individual lesion scores are used in drug treatment groups. In some cases, the observed treatment score is greater than the mean control value (exacerbation of lesion formation is not considered). In rare instances, the data from an animal will be discarded if, e.g., feces are found in the stomach.

In dose-response studies, the ED$_{50}$ (dose at which 50% inhibition of lesion formation occurs) is determined by probit analysis.

Indomethacin

Male Long Evans rats (approximately 275-300 gms) are housed 6 per cage and acclimated at least three days in a controlled environment while maintained on an ad libitum schedule of food and water. Prior to the experiment, rats are deprived of food for twenty-four hours and water for 1½ hours. On the day of the experiment, rats are randomly placed individually into a stainless steel cage with a wire mesh bottom. Control or drug treated groups consist of 5 rats each. Grouped rats receive a test drug or vehicle administered orally 30 or 60 minutes prior to the lesioning agent. Gastric lesions are induced by administration of indomethacin solution (30 mg/kg) by gavage (3.0 ml/kg). The indomethacin is prepared by dissolving 100 mg powder in 1.0 ml of 1N NaHCO$_3$ and heating until dissolved. Water is added to give a final indomethacin concentration of 10 mg/ml in 0.1N NaHCO$_3$. Four hours after indomethacin the rats are sacrificed by injecting T-61 euthanasia solution (Hoechst). To determine duration or mechanism of action, different times or routes of compound administration are used.

The stomachs are removed, opened along the curvature, rinsed with water and spread out flat in a standard position for examination and photographing.

Under the conditions described, indomethacin normally produces prominent macroscopic lesions in the fundic glandular secreting portion of the stomach.

Nonlesioned forestomach and other accessory tissues are trimmed off to improve standard placement. The remaining fundic tissue along with a millimeter reference scale is photographed at 2X actual size with a Polaroid camera with a close-up lens. Scoring of lesions is done from this permanent record.

For each animal the severity of gastric lesions is defined as the sum of the maximum continuous lengths of the lesions (in mm). Barely visible spots (petechia) are scored as 1.0 mm each and added to the total length. Real lesion length (mm) is obtained after dividing the total length score by two.

The mean lesion score is calculated for each treatment group. From this, the percent inhibition of lesion formation, I, is calculated:

$$I = \frac{\text{Lesion Score (controls)} - \text{Lesion Score (treated)}}{\text{Lesion Score (controls)}} \times 100$$

The mean lesion score for a control group will be used to calculate "I" but individual lesion scores will usually be used in drug treatment groups. Observed treatment scores that exceed the mean control value are taken as the mean control value without considering exacarbation of lesion formation.

In dose-response studies, the ED$_{50}$ (dose at which 50% inhibition of lesion formation occurs) is determined by probit analysis.

The results of the gastroprotective studies in the rat models with respect to ED$_{50}$ values (mg/kg) for the various irritants, by oral treatment, are summarized in Table III.

TABLE III

| Irritant | Metaproterenol | Cimetidine | Potency Ratio (Cimetidine = 1) |
|---|---|---|---|
| ETOH | 0.19 (0.03–0.47)* | 223 (191–256) | 1174 |
| Aspirin + Stress | 11.3 (7.29–16.2) | 4.5 (2.0–7.1) | 0.4 |
| HCl | 8.9 (4.4–17.8) | 225 (176–284) | 25.3 |
| Indomethacin | 2.0 (1.0–3.7) | 5.5 (3.9–7.3) | 2.8 |

*(95% confidence limit)

In three out of four tests, metaproterenol was more effective than cimetidine (potency ratio range 2.75–1174).

In view of the above test results, using metaproterenol which is a typical beta adrenergic agonist used commonly for testing such materials, beta adrenergic agonists are indicated as good gastroprotectant and antisecretory agents useful in the treatment of gastrointestinal disorders such as gastroesophageal reflux disease (GERD), dyspepsia, undue gastric acid secretion, gastritis and peptic ulcer.

The following Examples are given to further illustrate the present invention. It is to be understood, however, that this invention is not limited thereto.

EXAMPLES

|  | 1 | 2 | 3 | 4 |
|---|---|---|---|---|
| aspirin | 325 mg | 325 mg | 325 mg | 325 mg |
| metaproterenol | 3.33 mg | — | — | — |
| isoproterenol | — | 10 mg | — | — |
| albuterol | — | — | 2.67 mg | — |
| terbutaline | — | — | — | 1.67 mg |

To test the effectiveness of the beta adrenergic agonists in protecting the stomach against NSAID induced mucosal injury each beta adrenergic agonist is administered to dogs simultaneously and orally with, for example, aspirin in capsules. A standard dose of 975 mg of aspirin is administered with varying doses of the beta adrenergic agonist in a capsule and the stomach lining of the dogs were examined endoscopically and rated for the degree of injury.

All test formulations are prepared on the day of the tests. The capsules are placed in the back of the dog's throat. A catheter with attached funnel is positioned in the dog's stomach and 50ml of deionized water is administered.

Healthy adult beagle dogs of either sex are selected for testing. Dogs are housed individually in stainless steel cages with grid floors to allow excreta to pass through. Room temperature in the holding rooms and test laboratories is maintained between 65° F and 85° F and relative humidity of between 30% and 80%. Room lights remain on from 6:00 AM to 4:00 PM.

Each dog is trained to stand in a stanchion with sling support and to accept a bit tied in its mouth. A gastroscope is then passed through the bit into the dog's stomach. This training requires ten days to two weeks in most dogs.

To determine whether a dog is suitable for test purposes, its stomach is examined for a normal mucosa, and its gastric responsiveness to aspirin is evaluated (as under Test Procedure). An acceptable gastric irritation score in the antrum must be 5 or greater, 2 hours after dosage.

Food is withheld from test dogs for 24 hrs. before the test and during the test and water is allowed ad lib. The dogs are moved into a holding area away from the kennel. Fasted dogs of either sex are examined gastroscopically to ensure that their stomachs have normal healthy mucosal linings. The dogs are dosed orally with test formulations, which are flushed into their stomachs with 50 ml. of deionized water. They are then re-examined two hours later for gastric petechiae and signs of bleeding according to the following scale:

0 = uniform, pale to dark pink mucosa
1 = darker pink or blotchy mucosa
2 = petechias and/or light red streaks
3 = few small lesions
4 = many or connected small lesions (striations)
5 = few large lesions
6 = many large lesions
7 = massive hemorrhagic damage Severity of bleeding for each treatment and at each time is calculated as the mean gastric irritation score.

In addition to the endoscopic observation of the gastric mucosa of each dog a qualitative description of gastric fluid is recorded and a pH measurement is made of the gastric fluid. All of these are done 2 hours after administration of the test product.

A base line is established by measuring the various parameters after the administration of 975 mg of aspirin by itself. The resting stomach has an irritation score of 0 and a pH of 5 to 5.5. Aspirin alone produced injury which scored at approximately 5.5 after 2 hours and the gastric pH at this time is about 3.1. After 4 hours these values were 3.7 for the irritation factor and the pH was 4.8. This indicates that a certain amount of healing takes place between the 2nd and 4th hour after administration.

The results of the various tests are summarized in Table IV below.

TABLE IV

| Test Composition | 2 Hr. Score | |
|---|---|---|
|  | Injury | pH |
| aspirin (975 mg) | 5.6 | 3.1 |
| aspirin (975 mg) + isoproterenol (7.5 mg) | 3.8 | 3.5 |
| aspirin (975 mg) + isoproterenol (15 mg) | 2.7 | 3.8 |
| aspirin (975 mg) + isoproterenol (30 mg) | 1.3 | 5.0 |
| aspirin (975 mg) + terbutaline (1.25 mg) | 4.0 | 2.9 |
| aspirin (975 mg) + terbutaline (5.0 mg) | 1.4 | 4.0 |
| aspirin (975 mg) + terbutaline (10.0 mg) | 1.2 | 4.6 |
| aspirin (975 mg) + albuterol (8 mg) | 1.0 | 5.4 |
| aspirin (975 mg) + metaproterenol (20 mg) | 0.75 | 5.7 |

An examination of these data shows that the beta adrenergic agonists provide significant protection against aspirin induced mucosal injury particularly at the 2 hour level after administration. This protection, moreover, does not appear to be particularly related to the pH of the gastric contents.

What is claimed is:

1. A pharmaceutical composition for oral administration having reduced potential for NSAID-induced gastrointestinal injury comprising a therapeutically effective amount of NSAID and a protective quantity of a beta adrenergic agonist component selected from the group consisting of isoproterenol, metaproterenol, terbutaline, albuterol, fenoterol, bitolterol, isoetharine, colterol, ritodrine, and their pharmaceutically acceptable salts.

2. A composition according to claim 1 in which said beta adrenergic agonist component is isoproterenol.

3. A composition according to claim 1 wherein said beta adrenergic agonist component is terbutaline.

4. A composition according to claim 1 wherein said beta adrenergic agonist is albuterol.

5. A composition according to claim 1 wherein said beta adrenergic agonist is metaproterenol.

6. A composition as in any one of claims 1,2,3,4 or 5 in which said NSAID is aspirin.

7. A composition as in any one of claims 1,2,3,4 or 5 wherein said NSAID is ibuprofen.

8. A composition as in any one of claims 1,2,3,4 or 5 having a daily average dose of from about 10 mg/Kg/day to about 100 mg/Kg/day of said NSAID and from 0.0003 mg/Kg/day to about 500 mg/Kg/day of said beta adrenergic agonist component.

9. A composition as in any one of claims 1,2,3,4 or 5 in the form of unit dosage form containing from about 200 mg to about 600 mg of said NSAID and from about 0.7 mg to about 70 mg of said beta adrenergic agonist component.

10. A composition as in any one of claims 1,2,3,4 or 5 in which said NSAID is aspirin, the daily average dose of said aspirin being from about 10 mg/Kg/day to about 100 mg/Kg/day and of said beta adrenergic agonist being from about 0.0003 mg/Kg/day to about 500 mg/Kg/day.

11. A composition as in any one of claims 1,2,3,4 or 5 in the form of a unit dosage form containing from about 200 mg to out 600 mg of aspirin and from about 0.70 mg to about 70 mg of said beta adrenergic agonist component.

12. A composition as in any one of claims 1,2,3,4 or 5 in which said NSAID is ibuprofen, the daily average dose of said ibuprofen being from about 10 mg/Kg/day to about 100 mg/Kg/day and of said beta adrenergic agonist being from about 0.0003 mg/Kg/day to about 500 mg/Kg/day.

13. A composition as in any one of claims 1,2,3,4 or 5 in the form of unit dosage form containing from about 30 mg to about 300 mg of ibuprofen being from about 0.7 mg to about 70 mg of said beta adrenergic agonist component.

14. A composition as in any one of claims 1,2,3,4 or 5 having a daily average dose of from about 15 mg/kg/day to about 75 mg/kg/day of said NSAID and from about 0.01 mg/kg/day to about 10 mg/kg/day of said beta adrenergic agonist component.

15. A process for orally administering a therapeutically effective amount of an NSAID to a subject which comprises orally coadministering with said NSAID a gastroprotective amount of a beta adrenergic agonist component selected from the group consisting of isoproterenol, metaproterenol, terbutaline, albuterol, fenoterol, bitolterol, isoetharine, colterol, ritodrine, and their pharmaceutically acceptable salts, whereby the potential for NSAID-induced gastrointestinal injury in said subject is reduced.

16. A process according to claim 15 wherein the beta adrenergic agonist component is isoproterenol.

17. A process according to claim 15 wherein the beta adrenergic agonist component is terbutaline.

18. A process according to claim 15 wherein the beta adrenergic agonist component is albuterol.

19. A process according to claim 15 wherein the beta adrenergic agonist component is metaproteranol.

20. A process as in anyone of claims 15,16,17,18 or 19 wherein said NSAID is aspirin.

21. A process as in anyone of claims 15,16,17,18 or 19 wherein the NSAID is ibuprofen.

22. A process as in anyone of claims 15,16,17,18 or 19 wherein the average daily dose of said NSAID given to said subject is from about 10 mg/Kg/day to about 100 mg/Kg/day and the daily average dose of said beta adrenergic agonist component is from about 0.0003 mg/Kg/day to about 500 mg/Kg/day.

23. A process as in anyone of claims 15,16,17,18 or 19 wherein said NSAID and said beta adrenergic agonist component are administered as a unit dosage form containing from about 200 mg to about 600 mg of NSAID and from about 0.7 mg to about 70 mg of said beta adrenergic agonist component.

24. A process as in anyone of claims 15,16,17,18 or 19 in which said NSAID is aspirin, the daily average dose of said aspirin being from about 10 mg/Kg/day to about 100 mg/Kg/day and said beta adrenergic agonist being from about 0.0003 mg/Kg/day to about 500 mg/Kg/day.

25. A process as in anyone of claims 15,16,17,18 or 19 wherein the composition is employed in the form of a unit dosage form containing from about 200 mg to about 600 mg of aspirin and from about 0.7 mg to about 70 mg of said beta adrenergic agonist component.

26. A process as in anyone of claims 15,16,17,18 or 19 in which said NSAID is ibuprofen, the daily average dose of said ibuprofen being from about 10 mg/Kg/day to about 100 mg/Kg/day and of said beta adrenergic agonist being from about 0.0003 mg/Kg/day to about 500 mg/Kg/day.

27. A process as in anyone of claims 15,16,17,18 or 19 wherein the composition is employed in the form of a unit dosage form containing from about 30 mg to about 300 mg of ibuprofen and from about 0.7 mg to about 70 mg of said beta adrenergic agonist component.

28. A process as in anyone of claims 15,16,17,18 or 19 wherein the average daily dose is from about 15 mg/kg/day to about 75 mg/kg/day of said NSAID and from about 0.01 mg/kg/day to about 10 mg/kg/day of said beta adrenergic agonist component.

29. The process according to claim 28 wherein the NSAID is aspirin.

30. The process according to claim 28 wherein the NSAID is ibuprofen.

* * * * *